United States Patent [19]

Hussain

[11] 4,120,958

[45] Oct. 17, 1978

[54] NOVEL 2-ACETOXYBENZOIC ACID-NICOTINAMIDE COMPLEXES

[75] Inventor: Anwar A. Hussain, Lexington, Ky.

[73] Assignee: Interx Research Corporation, Lawrence, Kans.

[21] Appl. No.: 776,933

[22] Filed: Mar. 11, 1977

[51] Int. Cl.$^2$ ............... A61K 31/625; C07D 213/81; C07D 213/82
[52] U.S. Cl. ............... 424/232; 260/295 AM; 260/295.5 A
[58] Field of Search ............... 260/295 AM, 295.5 A; 424/232

[56] References Cited

U.S. PATENT DOCUMENTS 3,312,593  4/1967  Sheen ............... 424/232

OTHER PUBLICATIONS

Cazaux et al., Chem. Abst. vol. 67, 1967, parag. 1114502.

*Primary Examiner*—Natalie Trousof
*Assistant Examiner*—Cary Owens
*Attorney, Agent, or Firm*—Bacon & Thomas

[57] ABSTRACT

There is provided, a novel 2-acetoxybenzoic acid-nicotinamide complex, which exhibits enhanced water solubility and dissolution characteristics, thus permitting rapid absorption of the 2-acetoxybenzoic acid through the gastrointestinal lining for attainment of exceptional 2-acetoxybenzoic acid blood levels.

10 Claims, No Drawings

NOVEL 2-ACETOXYBENZOIC ACID-NICOTINAMIDE COMPLEXES

BACKGROUND OF THE INVENTION

1. Field of the Invention

The present invention relates to 2-acetoxybenzoic acid and more particularly, the present invention relates to therapeutically useful complexes of 2-acetoxybenzoic acid, i.e., 2-acetoxybenzoic acid-nicotinamide or isonicotinamide complexes.

The novel complexes of this invention exhibit analgesic, antipyretic, and antirheumatic therapeutic activity.

The compound, 2-acetoxybenzoic acid, is commonly known as "aspirin" and/or "acetylsalicylic acid", and is one of the most widely used compounds in the treatment of simple pain and inflammation. 2-acetoxybenzoic acid is widely employed as an analgesic, an antipyretic, an anti-inflammatory and an antirheumatic agent, and it is particularly useful in the relief of fever, headache, myalgia, arthralgia and other pains associated with integumental structures. 2-Acetoxybenzoic acid is generally administered for these conditions in the form of a powder, particle, capsule, solution, tablet or other pharmaceutically acceptable dosage form because it is advantageous from the standpoint that chronic use of the compound will not lead to a tolerance or addiction thereof. Moreover, its toxicity is much lower than most compounds possessing similar pharmacologic activity. See, THE PHARMACOLOGICAL BASIS OF THERAPEUTICS, by Goodman and Gilman, Fourth Edition, page 316, 1970 (The MacMillan Company, New York, New York). However, 2-acetoxybenzoic acid, as used for these purposes, is well-known by the practicing skilled artisan of the medical arts to exhibit certain unwanted and deliterious side effects. Specifically, it induces occult hemorrhaging in the gastrointestinal tract, which results from contact of the insoluble solid particulate of the compound with the gastrointestinal mucosa. As a result of this insolubilization, particles of 2-acetoxybenzoic acid will adhere to the gastrointestinal mucosa in the form of crystals and such crystals, taken together with the acidic environment of the gastrointestinal lining, will produce microetching thereof, which in turn, leads to gastrointestinal bleeding. See, J. Pharm. Sci., Vol. 58, pgs 1277–1279, 1969; Clin. Pharm. and Therap., Vol. 10, pgs 400–408, 1969; J. Pharm. Sci., Vol. 10, pgs 1511–1513, 1970; British Medical Journal, Vol. 3, pgs 545–547, 1972; Archives of Internal Medicine, Vol. 129, pgs 457–460, 1972; and Clin. Pharm. and Therap., Vol. 14, No. 1, pgs 62–66, 1973.

2. Description of the Prior Art

To date, it is known that gastric bleeding can be diminished if (1) an aqueous solution of 2-acetoxybenzoic acid is administered or (2) a buffered aqueous solution of 2-acetoxybenzoic acid is administered. However, such solutions leave much to be desired in that they are commercially and consumer-wise unacceptable, i.e., water and/or buffered solutions are unacceptable as a suitable pharmaceutical dosage form.

One product on the market, commercially known as "Alka-Seltzer ®" is basically an alkaline effervescent 2-acetoxybenzoic acid formulation, which does exhibit satisfactory water solubility and dissolution, insofar as 2-acetoxybenzoic acid is concerned. However, at least three disadvantages are associated with this product. Firstly, the product is contained in a tablet form and must initially be dissolved in water prior to consumption. Secondly, because the product contains a high amount of sodium ion, it is unacceptable for administration to hypertensive patients (those who suffer from high blood pressure), because it has now been medically established that the sodium ion contributes to hypertension. Thirdly, the alkaline nature of the product per se alters the pH of the blood and urine to the alkaline side. Chronic use of this product could thus initiate alkalosis.

Finally, U.S. Pat. No. 3,312,593 discloses an anti-inflammatory composition, which comprises a physical mixture of 2-acetoxybenzoic acid and nicotinic acid; however, this patent is solely concerned with the recognition that these two compounds, in "admixture" can relieve inflammation and edema. In addition, this reference is strictly concerned with an "admixture" of 2-acetoxybenzoic acid and nicotinic acid and does not concern itself with a "complex" thereof. Moreover, nicotinic acid will cause flushing at the extremities.

SUMMARY OF THE INVENTION

Accordingly, it is one object of the present invention to provide a 2-acetoxybenzoic acid complex which will exhibit enhanced water solubility when compared to 2-acetoxybenzoic acid per se.

It is another object of the present invention to provide a 2-acetoxybenzoic acid complex which will exhibit enhanced dissolution values in aqueous solution when compared to 2-acetoxybenzoic acid per se.

Still, it is another object of the present invention to provide a 2-acetoxybenzoic acid complex which will permit 2-acetoxybenzoic acid to be rapidly solubilized and dissociated in the gastrointestinal tract for the purpose of permitting total absorption of the 2-acetoxybenzoic acid through the gastrointestinal lining, thus eliminating gastrointestinal bleeding.

Furthermore, it is another object of the present invention to provide a 2-acetoxybenzoic acid complex, which can be formulated in a suitable oral pharmaceutically acceptable dosage form for administration as an analgesic, an antipyretic, an anti-inflammatory and an antirheumatic agent to warm-blooded animals.

Finally, it is yet another object of the present invention to provide a 2-acetoxybenzoic acid complex which will permit all the above objectives to be attained and yet, render the complexing moiety of the 2-acetoxybenzoic acid complex (nicotinamide portion) nontoxic, even when metabolized. Nicotinamide has recognized therapeutic activity. See, Merck Index (Ninth Edition), p. 6336.

These and other objects of the instant invention will become more readily apparent from a reading of the accompanying disclosure and appended claims thereto.

The foregoing objects are attained with the use of novel 2-acetoxybenzoic acid-nicotinamide complexes of the formula:

$$A \cdot N_{(x)}$$

wherein $A$ represents 2-acetoxybenzoic acid; $N$ represents a member selected from the group consisting of nicotinamide and isonicotinamide; and $(x)$ represents an integer of about 2.

At this point, it should be emphasized that the formula noted above actually represents a true chemical complex of 2-acetoxybenzoic acid with the appropriate nicotinamide derivative and does not represent a true chemical compound as understood by the skilled artisan.

It also should be emphasized that nicotinamide and isonicotinamide are interchangeable as complexing agents with the 2-acetoxybenzoic acid in the overall complex disclosed and claimed herein.

With reference to "x", the definition thereof as an integer of about 2 is meant to specify that the ratio of 2-acetoxybenzoic acid to the nicotinamide derivative employed will range somewhere from 1:1 to 1:2.

DETAILED DESCRIPTION OF THE INVENTION

The complex described above can be prepared by a simple step-wise procedure as explained hereinafter. Firstly, when preparing the complex at room temperature (25° C.), on a non-limiting basis, equal amounts of reagent grade nicotinamide or isonicotinamide and reagent grade 2-acetoxybenzoic acid are mixed with stirring in an appropriate amount of a suitable solvent, such as water, methanol, ethanol, isopropanol, butanol, dioxane, and the like until a clear solution is obtained. Next, the solution is filtered if necessary and then cooled to around 10° C. to produce crystals of the isolated complex.

When preparing the complex at temperatures above room temperature the following procedure can be employed.

On a nonlimiting basis, equal amounts of reagent grade nicotinamide of isonicotinamide and reagent grade 2-acetoxybenzoic acid are admixed, with stirring, in a suitable solvent, as described above until a clear solution is obtained. The solution, if necessary, is then filtered and then, stirring is re-commenced at room temperature until the complex is formed. The complex is then filtered and dried in vacuo at 37° C. In this procedure, as an optional embodiment, the filtrate can be recycled with one-half of the original amount of nicotinamide or isonicotinamide and 2-acetoxybenzoic acid employed to produce more of the complex.

When preparing the complex at room temperature, normally, the amount of solvent required will be about 5 times that required for preparing the complex at temperatures above room temperature. Naturally, in either method of preparation, standard pressure is employed.

When operating above room temperature, the amount of each compound and solvent required to prepare a 1 kg. batch of the complex is as follows:

| Solvent | 6400 ml |
|---|---|
| 2-acetoxybenzoic acid | 1000 g |
| Nicotinamide or isonicotinamide | 1000 g |

Broadly speaking, the method of preparation of the complex can be carried out at temperatures approximating room temperature or above in accordance with the above outlined procedures. However, when operating above room temperature, a preferred temperature range of from 26° C. to 80° C. is suggested and most preferred, is a temperature range of from 43° C. to 45° C. Naturally, with the latter temperature range, the second preparatory method noted above would be employed.

A better understanding of the present invention will be gained from the following examples, which examples are merely intended to be illustrative and nonlimitative of the present invention.

EXAMPLE I

In accordance with the analytical procedure outlined by J. W. Poole, *Drug Inform. Bull.*, Vol. 3, page 8, 1960, dissolution studies were made with commercially available 2-acetoxybenzoic acid per se and the 2-acetoxybenzoic acid-nicotinamide complex of the instant invention, wherein the ratio of 2-acetoxybenzoic acid to nicotinamide was 1:2.

The 2-acetoxybenzoic acid-nicotinamide complex was prepared as follows. 25 g of reagent grade nicotinamide, 25 g of 2-acetoxybenzoic acid and 160 ml of isopropanol were stirred at 43° to 45° C., at standard pressure, for a period of from 5 to 10 minutes whereby a clear solution was obtained. Then, the temperature of the solution was lowered to 24° C. and the solution was continually stirred for approximately 2 hours until the 2-acetoxybenzoic acid-nicotinamide formed. The complex was then filtered and dried in vacuo at 37° C. The IR analysis, elemental analysis, and chemical analysis of the isolated complex was consistent with the complex obtained (ratio of 1:2 with respect to 2-acetoxybenzoic acid and nicotinamide). The yield of the complex was 25 g.

Next, the complex (500 mg, of which 280 mg was 2-acetoxybenzoic acid) obtained was compared with 2-acetoxybenzoic acid per se (300 mg) for solubility and dissolution rate in 500 ml of simulated gastric juice (0.1 N HCl acid) the results of which are set forth in Table I below:

TABLE I

| TIME (Minutes) | % of 2-acetoxybenzoic acid dissolved | % of complex dissolved |
|---|---|---|
| 2 | 0 | 100 |
| 5 | 5 | |
| 10 | 15 | |
| 30 | 30 | |
| 60 | 75 | |

EXAMPLE II

In accordance with the procedure outlined in Example I, the isonicotinamide complex of 2-acetoxybenzoic acid is obtained. When tested against 2-acetoxybenzoic acid per se for solubility and dissolution rate, results substantially similar to those obtained in Table I are observed.

EXAMPLE III

Two tablets, labelled "A" and "B", respectively, were formulated as follows:

Tablet "A" comprised 500 mg of the 2-acetoxybenzoic acid-nicotinamide complex of this invention, 200 mg of soluble starch, and 0.25 mg of magnesium stearate.

Tablet "B" contained 500 mg of 2-acetoxybenzoic acid-isonicotinamide complex of this invention; 200 mg of soluble starch; and 0.25 mg of magnesium stearate.

A third tablet, tablet "C", was a commercially available 2-acetoxybenzoic acid tablet, containing 300 mg of 2-acetoxybenzoic acid.

At this point, it should be mentioned, that 500 mg of the 2-acetoxybenzoic acid complex contained in tablets "A" and "B" contain approximately 300 mg of 2-acetoxybenzoic acid. Accordingly, in terms of 2-acetoxybenzoic acid content, tablets "A" through "C" were identical.

Each tablet, "A" through "C" was introduced into 500 ml of simulated gastric juice (0.1 N HCl solution).

Tablets "A" and "B", respectively, completely dissolved and disassociated within two minutes, providing 100% solubility. Tablet "C", after 30 minutes, only solubilized and disassociated to the extent of 80%.

With respect to tablets "A" and "B", the ratio of 2-acetoxybenzoic acid to nicotinamide and iso-nicotinamide, respectively was 1:2.

The complexes of this invention are suitably administered in oral dosage form, such as by tablet or capsule, by combining the same in a therapeutic amount (e.g., dosage regimen for aspirin on an equivalent weight basis) with any oral pharmaceutically acceptable inert carrier, such as lactose, starch (pharmaceutical grade), dicalcium phosphate, calcium sulfate, Kaolin, Mannitol, and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethyleneglycol, ethylcellulose and waxes. Typical lubricants for use in these dosage forms can include, without limitation, boric acid, sodium benzoate, sodium acetate, sodium chloride, leucine and polyethyleneglycol. Suitable disintegrators can include, without limitation, starch, methylcellulose, agar, bentonite, cellulose and wood products, alginic acid, guar gum, citris pulp, carboxymethylcellulose and sodium lauryl sulfate. If desired, a conventionally pharmaceutically acceptable dye can be incorporated into the dosage unit form, i.e., any of the standard FD&C dyes.

Any skilled artisan can prepare these oral dosage forms by simply referring to the oral dosage form preparatory procedure outlined in "REMINGTON'S PHARMACEUTICAL SCIENCES," Fourteenth Edition (1970), pages 1659 through 1698 inclusive.

The dose administered, whether a single dose or a daily dose, will, of course, vary with the needs of the individual being treated. However, the dosage administered is not subject to definite bounds, but it will usually be an effective therapeutic amount, or the equivalent on a molar basis of the pharmacologically active form produced upon the metabolic release of the active drug (2-acetoxybenzoic acid) to achieve its desired pharmacological or physiological effect.

Summarizing then, the complexes of the present invention offer superior results over 2-acetoxybenzoic acid per se from the standpoint that these complexes permit 2-acetoxybenzoic acid to be released in highly soluble and disassociated form, thus permitting extremely high blood levels to be obtained and yet, the complexing agent (nicotinamide of iso-nicotinamide) remains as a nontoxic moiety, which will be metabolized into nontoxic byproducts.

Although the present invention has been adequately described in the foregoing specifications and examples included therein, it is obviously apparent that various changes and/or modifications can be made thereto by the skilled artisan without departing from the scope thereof. Such changes and/or modifications are properly, equitably and intended to be within the full range of equivalence of the following claims.

What I claim is:

1. A 2-acetoxybenzoic acid complex of the formula:

$$A \cdot N_{(x)}$$

wherein $A$ represents 2-acetoxybenzoic acid; wherein $N$ represents a member selected from the group consisting of nicotinamide and iso-nicotinamide; and wherein $(x)$ represents an integer of about 1:1 to 1:2.

2. The complex of claim 1, wherein $N$ represents nicotinamide.

3. The complex of claim 1, wherein $N$ represents isonicotinamide.

4. The complex of claim 1, wherein the ratio of 2-acetoxybenzoic acid to $N$ is about 1:2.

5. A method for inducing an analgesic, antipyretic and anti-inflammatory response in a warm-blooded animal, which comprises:
   orally administering thereto a safe and effective amount of a complex of the formula:

$$A \cdot N_{(x)}$$

wherein $A$ represents 2-acetoxybenzoic acid; wherein $N$ represents a member selected from the group consisting of nicotinamide and iso-nicotinamide; and wherein $(x)$ represents an integer of about 1:1 to 1:2, said complex being administered in combination with a pharmaceutically acceptable inert diluent.

6. The method of claim 4, wherein $N$ in the formula $A \cdot N_{(x)}$ represents nicotinamide.

7. The method of claim 4, wherein $N$ in the formula $A \cdot N_{(x)}$ represents iso-nicotinamide.

8. A pharmaceutical composition for oral administration to a warm-blooded animal comprising:

(1) a safe and effective amount of a complex of the formula:

$$A \cdot N_{(x)}$$

wherein $A$ represents 2-acetoxybenzoic acid; wherein $N$ represents a member selected from the group consisting of nicotinamide and iso-nicotinamide; and wherein $(x)$ represents an integer of about 1:1 and 1:2;

(2) a pharmaceutically acceptable inert diluent.

9. The composition of claim 8, wherein $N$ in the formula $A \cdot N_{(x)}$ represents nicotinamide.

10. The composition of claim 8, wherein $N$ in the formula $A \cdot N_{(x)}$ represents iso-nicotinamide.

* * * * *